US011850137B2

(12) United States Patent
Ashkenazi

(10) Patent No.: US 11,850,137 B2
(45) Date of Patent: Dec. 26, 2023

(54) INTRA-AORTIC DEVICE

(71) Applicant: Keystone Heart Ltd., Caesarea (IL)

(72) Inventor: Amit Ashkenazi, Caesarea (IL)

(73) Assignee: Keystone Heart Ltd., Caesarea (IL)

( * ) Notice: Subject to any disclaimer, the term of this patent is extended or adjusted under 35 U.S.C. 154(b) by 142 days.

(21) Appl. No.: 17/652,665

(22) Filed: Feb. 25, 2022

(65) Prior Publication Data

US 2022/0183814 A1   Jun. 16, 2022

Related U.S. Application Data

(63) Continuation of application No. 16/083,870, filed as application No. PCT/EP2017/055721 on Mar. 10, 2017, now abandoned.

(60) Provisional application No. 62/306,454, filed on Mar. 10, 2016.

(51) Int. Cl.
*A61F 2/01* (2006.01)

(52) U.S. Cl.
CPC .......... *A61F 2/01* (2013.01); *A61F 2/011* (2020.05); *A61F 2220/0008* (2013.01); *A61F 2230/0008* (2013.01); *A61F 2230/0013* (2013.01); *A61F 2230/0043* (2013.01); *A61F 2230/0095* (2013.01); *A61F 2250/0098* (2013.01)

(58) Field of Classification Search
CPC .... A61F 2/01; A61F 2/011; A61F 2230/0008; A61F 2230/0013; A61F 2230/0095; A61F 2220/0008; A61F 2250/0098
See application file for complete search history.

(56) References Cited

U.S. PATENT DOCUMENTS

| 7,896,899 | B2 | 3/2011 | Patterson et al. |
| 9,339,367 | B2* | 5/2016 | Carpenter ............... A61F 2/013 |
| 9,370,438 | B2 | 6/2016 | Ginn |
| 10,076,400 | B2* | 9/2018 | Krahbichler ............. A61F 2/01 |
| 10,182,822 | B2* | 1/2019 | Freudenthal ...... A61B 17/12022 |
| 2001/0039450 | A1 | 11/2001 | Pavcnik et al. |
| 2007/0191884 | A1 | 8/2007 | Eskridge et al. |
| 2008/0065145 | A1* | 3/2008 | Carpenter ................. A61F 2/01 |
| | | | 606/200 |
| 2010/0179583 | A1 | 7/2010 | Carpenter et al. |
| 2010/0179585 | A1 | 7/2010 | Carpenter et al. |
| 2010/0179647 | A1* | 7/2010 | Carpenter ................. A61F 2/01 |
| | | | 623/2.11 |

(Continued)

FOREIGN PATENT DOCUMENTS

| WO | WO 2000044308 A2 | 8/2000 |
| WO | WO 2000044308 A3 | 8/2000 |

(Continued)

OTHER PUBLICATIONS

WIPO, European International Search Authority, International Search Report and Written Opinion dated May 12, 2017 in International Patent Application No. PCT/EP2017/055721, 13 pagSep. 7, 2018.

(Continued)

*Primary Examiner* — Phong Son H Dang

(57) ABSTRACT

An intra-aortic device comprising a filter and a frame defining the shape of the filter, wherein the frame is intrinsically curved in a superior direction by a proximal superior bend and/or a distal superior bend, whereupon installation in an aorta, the M frame flattens.

21 Claims, 6 Drawing Sheets

(56) References Cited

U.S. PATENT DOCUMENTS

| | | | |
|---|---|---|---|
| 2011/0295303 A1 | 12/2011 | Freudenthal | |
| 2011/0295304 A1 | 12/2011 | Jonsson | |
| 2013/0218194 A1* | 8/2013 | Jonsson | A61B 17/12172 606/200 |
| 2014/0074152 A1 | 3/2014 | Shezifi et al. | |
| 2015/0257868 A1 | 9/2015 | Shezifi | |
| 2015/0313701 A1 | 11/2015 | Krahbichler | |
| 2016/0100928 A1 | 4/2016 | Lees et al. | |
| 2016/0106531 A1 | 4/2016 | Shezifi | |
| 2016/0175084 A1* | 6/2016 | Johnson | A61F 2/0103 606/200 |
| 2016/0175085 A1* | 6/2016 | Johnson | A61F 2/0103 606/200 |
| 2016/0262864 A1* | 9/2016 | Von Mangoldt | A61F 2/01 |
| 2016/0302909 A1* | 10/2016 | Kelly | A61F 2/01 |
| 2016/0324621 A1 | 11/2016 | Shezifi et al. | |
| 2017/0189160 A1 | 7/2017 | Krahbichler | |

FOREIGN PATENT DOCUMENTS

| | | |
|---|---|---|
| WO | WO 2014145598 A1 | 9/2014 |
| WO | WO2014/188410 A2 | 11/2014 |

OTHER PUBLICATIONS

European Patent Office, Extended European Search Report dated Jul. 25, 2022 in European Patent Application No. 22168897.1, 7 pages.

\* cited by examiner

INTRA-AORTIC DEVICE

RELATED APPLICATIONS

This application is a continuation of and claims priority to U.S. patent application Ser. No. 16/083,870 filed Sep. 7, 2018 entitled Intra-Aortic Device, which is the U.S. National phase of and claims priority to International Patent Application Serial No. PCT/EP2017/055721, International Filing Date Mar. 10, 2017, entitled Intra-Aortic Device, which claims benefit of and priority to U.S. Provisional Application Ser. No. 62/306,454 filed Mar. 10, 2016 entitled Intra-Aortic Device And Method, all of which are hereby incorporated herein by reference in their entireties.

BACKGROUND OF THE INVENTION

Field of the Invention

The present disclosure relates to intra-aortic devices and methods to prevent emboli from entering arteries branching from the aorta, e.g., arteries that lead to the brain.

Description of the State of the Art

Various medical procedures may perturb blood vessels or surrounding tissues. When this occurs, potentially harmful particulates, such as emboli, may be released into the blood stream. These particulates can be damaging, e.g., if they restrict blood flow to the brain. Devices to block or divert particulates from flowing into particular regions of the vasculature have been proposed but may not eliminate the risks associated with the release of potentially harmful particulates into the blood stream during or after particular medical procedures.

Improved devices for blocking or diverting vascular particulates are under development, but each intravascular procedure presents unique risks.

As intravascular devices and procedures, such as transcatheter aortic valve implantation (TAVI), become more advanced, there is an emerging need for features that provide these devices with improved ease of use, intravascular stability, and embolic protection.

Possible areas of improvements of such devices and procedures include "windsailing" of devices with pulsatile blood flow, leakage of fluid and/or particulate matter at peripheral portions of devices during use thereof, secure positioning in a patient during use and/or retrievability, etc.

Hence, an improved intravascular device, system and/or method would be advantageous and in particular allowing for increased flexibility, cost-effectiveness, and/or patient safety would be advantageous.

SUMMARY OF THE DISCLOSURE

Accordingly, embodiments preferably seek to mitigate, alleviate or eliminate one or more deficiencies, disadvantages or issues in the art, such as the above-identified, singly or in any combination according to the features of the appended independent patent claims.

In a first aspect, the present disclosure includes an intra-aortic device including a filter and a frame defining the shape of the filter, wherein the frame is intrinsically curved in a superior direction, by one or more portions of the frame having a superior bend, such as a superior distal bend and/or a superior proximal bend, whereupon installation in an aorta, the frame flattens. In some examples, the frame is intrinsically curved with a radius of curvature from about 1 cm to 25 cm (e.g., 1, 2, 3, 4, 5, 6, 7, 8, 9, 10, 11, 12, 13, 14, 15, 16, 17, 18, 19, 20, 21, 22, 23, 24, or 25 cm); or is alternatively or in addition a composite of various degrees of curvature.

In one example, the frame flattens upon installation in an aorta.

In another example, the filter is alternatively or in addition configured to span more than one artery branching from the aorta (e.g., the innominate (brachiocephalic) artery, the left common carotid artery, and/or the left subclavian artery).

In another example, the frame is alternatively or in addition configured to be held in contact with both a portion at an ascending aorta and a portion at a descending aorta, simultaneously (e.g., upon installation in an aorta, e.g., an aortic arch).

In another example, the superior face of the frame or filter is configured alternatively or in addition to contact a wall of the ascending aorta and/or a wall of the descending aorta (e.g., upon installation in an aorta, e.g., an aortic arch).

In one example, the frame comprises alternatively or in addition one or more superior stabilizers and/or one or more inferior stabilizers.

In some examples, the frame has a superior stabilizer, a front inferior stabilizer, and a back inferior stabilizer.

In some examples, the superior stabilizer is attached to the frame at a front portion and a back portion of the frame.

In some examples, the superior stabilizer is configured to contact a proximal wall of an innominate artery (e.g., upon installation in an aorta, e.g., an aortic arch).

In some examples, the superior stabilizer is attached to the frame at a position proximal to the innominate artery (e.g., upon installation in an aorta, e.g., an aortic arch).

In some examples, the superior stabilizer comprises one or more (e.g., 1, 2, 3, 4, 5, 6, or more) intrinsic proximal bends.

In some examples, the one or more intrinsic proximal bends are configured to optimize contact of the superior stabilizer (e.g., at a transverse curve or elsewhere) with the proximal wall of the innominate artery.

In some examples, the superior stabilizer comprises four intrinsic proximal bends.

In some examples, two intrinsic proximal bends define the front end and the back end of a transverse curve.

In some examples, the front inferior stabilizer and the back inferior stabilizer contact a wall of the aorta (e.g., upon installation in an aorta, e.g., an aortic arch).

In some examples, the inferior stabilizers are attached to the frame at a position proximal to the ascending aorta (e.g., upon installation in an aorta, e.g., an aortic arch).

In some examples, the superior stabilizer is attached to the frame at a position distal to the attachment of the front inferior stabilizer or back inferior stabilizer.

In some examples, the filter is configured to block or divert emboli from passage into one or more arteries branching from the aorta (e.g., upon installation in an aorta, e.g., an aortic arch).

In some examples, the filter has a plurality of woven fibers.

In some examples, the filter comprises pores having a median pore size of less than about 5 mm (e.g., 5.0 mm, 4.5 mm, 4.0 mm, 3.5 mm, 3.0 mm, 2.5 mm, 2.0 mm, 1.5 mm, 1.0 mm, 900 µm, 800 µm, 700 µm, 600 µm, 500 µm, 400 µm, 300 µm, 200 µm, 100 µm, 50 µm, or less).

In some examples, the frame, the filter, or the stabilizers are made of nitinol.

In some examples, the proximal end of the frame is connected to a catheter.

In some examples, the frame is collapsible along a longitudinal axis (e.g., to fit within a tube having a radius of e.g. 1 mm, 2 mm, 3 mm, 4 mm, 5 mm, 6 mm, 7 mm, 8 mm, 9 mm, or 10 mm, e.g., to accommodate delivery to the aorta via an introducer sheath).

In another aspect, the disclosure features a method of preventing passage of emboli from an aorta into an artery branching from the aorta comprising installing a device of the disclosure in the aorta.

Definitions

As used herein, directional terms describing the device of the disclosure are interpreted as though the device is installed in an aorta, unless explicitly noted otherwise (e.g., by describing an intrinsic shape or feature).

As used herein, "intrinsic," or "intrinsically," refers to a material property that is independent from external factors, e.g., external forces. An intrinsic curve is curved when it is in a relaxed state (e.g., unconstrained by a luminal wall, e.g., of a delivery tube or a blood vessel. A portion of the frame may intrinsically curve the filter (e.g., in a superior direction), meaning that the filter's curvature results from an intrinsic property of that portion of the frame (e.g., a superior intrinsic bend).

As used herein, "installation in an aorta," or "installed in an aorta" is meant that the device is set in its intended functional position within an aorta, e.g., such that emboli are prevented from passing into a branching vessel.

As used herein, to "flatten" means to reduce or invert curvature. For example, a bend having an intrinsic radius of curvature of 5 mm is said to flatten when it is forced to reduce in curvature to a radius of curvature of 10 mm. A bend also flattens if it is forced to become substantially straight or to bend in the opposite direction of its initial curvature.

As used herein, to "optimize contact" means to increase the force, area, or position of contact (e.g., of a superior stabilizer to a wall of an innominate artery).

As used herein, "horizontal plane of the filter" refers to the plane of the filter running substantially horizontally when the filter is positioned within an aorta.

A portion of the filter may intrinsically, wholly or partially, take a planar shape (e.g., a substantially horizontal planar shape). The horizontal plane of the filter may be disposed between two intrinsically curved portions of the filter (e.g., a proximal superior bend and a distal superior bend).

As used herein, "central" or "central portion of the frame" refers to the portion of frame from about 10% proximal to the distal end of the frame to about 10% distal to the proximal end of the frame.

As used herein, the term "sagittal" refers to a plane spanning front-to-back and head-to-toe of a patient, and any parallel plane thereof.

As used herein, the term "coronal" refers to a plane spanning left-to-right and head-to-toe of a patient, and any parallel plane thereof.

As used herein, the term "transverse" refers to a plane spanning left-to-right and front-to-back of a patient, and any parallel plane thereof.

As used herein, "superior," or "superiorly" refers to the direction above a horizontal plane of the filter (i.e., towards the head, when positioned in an aorta). As used herein, to "bend superiorly" is to bend such that a substantially horizontal member (e.g., a portion of the frame) curves upward (i.e., towards the head of a subject) from the horizontal plane (i.e., in a superior direction) such that the member (e.g., a portion of the frame) is concave up.

As used herein, "inferior" or "inferiorly" refers to the direction below the horizontal plane of the filter (i.e., towards the feet, when positioned in an aorta). As used herein, to "bend inferiorly" is to bend such that a substantially horizontal member (e.g., a portion of the frame) curves downward from the horizontal plane (i.e., in an inferior direction) such that the member (e.g., a portion of the frame) is concave down.

As used herein, "distal" refers to a position within the aorta that is closer to the heart relative to a reference position. When the device is positioned in an aorta, the filter is on the distal end of the device.

As used herein, "proximal" refers to a position within the aorta that is further from the heart relative to a reference position. When the device is positioned in an aorta, the catheter is attached to the proximal end of the frame. Blood flows in a distal-to-proximal direction in the aorta.

As used herein, "catheter" refers to any wire, tube, delivery system, or elongated member used in interventional cardiology to introduce foreign objects (e.g., surgical tools) to a treatment site. As used herein, "patient" refers to a mammal (e.g., a human).

BRIEF DESCRIPTION OF THE DRAWINGS

The following drawings are illustrative of particular examples of the present disclosure and are not limiting the various examples encompassed by the present disclosure.

DETAILED DESCRIPTION OF THE DISCLOSURE

Figure 1A:
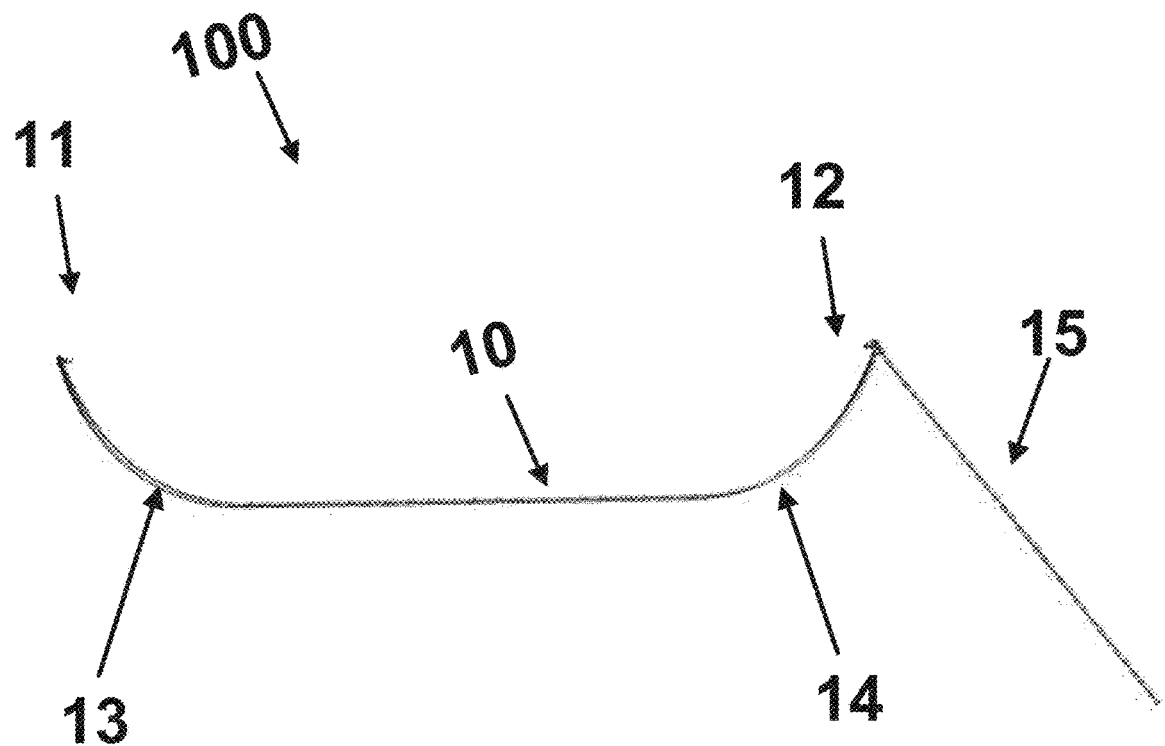
FIGS. 1A and 1B are schematic diagrams illustrating a frame and catheter attachment in an intrinsic configuration.

The present disclosure relates to intravascular devices and methods of using devices for intravascular procedures. Intravascular surgical procedures are performed for various indications, such as, aortic valve replacement. These procedures present significant risks as a result of perturbing particulates (e.g., blood clots, calcified debris, and emboli). Dislodged particulates (e.g., emboli) can flow downstream and impede circulation to vital organs, such as the brain (e.g., by flowing into the left subclavian artery, left common carotid artery, or innominate artery). Intravascular filters can be used to block or divert particulates (e.g., emboli) resulting from intravascular procedures. The present disclosure provides a device configured to prevent emboli from entering vessels that supply blood to the brain.

In general, the disclosure includes devices and methods including an intra-aortic device including a filter and a frame defining the shape of the filter. In some examples, the frame may be flat before being deployed in an aorta, such as in an aortic arch. Alternatively, in some examples, the frame may be, in some examples, intrinsically curved in a superior direction by one or more portions of the frame having a superior bend, e.g., a proximal superior bend and/or a distal superior bend.

This device can be installed in an aorta, e.g., an aortic arch, such that the frame flattens, e.g., becomes inferiorly concave.

Devices

The disclosure features an intra-aortic device having a filter attached to a frame that defines the shape of the filter. The frame is flexible, e.g., collapsible along a longitudinal axis for delivery to the aortic arch via an introducer sheath, according to methods described herein or known in the art.

The frame may in some example be of circular, elongated, substantially elliptical, and/or oblong. The frame is configured to flatten during installation in an aorta, e.g., at the aortic arch, to block the flow of emboli from the aorta to an artery branching from the aortic arch (e.g., innominate (brachiocephalic) artery, left common carotid artery, or left subclavian artery). The frame may be configured to be held in contact with both an ascending aorta and a descending aorta, simultaneously. The frame may be made from, for example, a single wire, a single twined wire; more than one twined wires, or a spring ring.

The frame may in some example be a circular, spring ring wire. In some examples, a circular, spring ring frame may be made into, for example, an elongated shape, substantially elliptical, or oblong. A frame made from a spring ring may improve positioning and self-alignment of the device in the aortic arch. A device made from a spring ring may also improve the force of the frame against the walls of the aortic arch, giving an improved self-stabilizing effect as a result.

In some examples, the frame may be flat before being deployed in an aorta, such as in an aortic arch. Alternatively, or in addition, shape memory properties may be used to provide a change of shape in the body to provide a tension and force of the frame against the inner aortic wall tissue. The shape memory effect may be triggered by body temperature, e.g. from a substantially flat shape to e.g. the shape shown in FIGS. 1A, B, 2A, B, 4 and 6. Insertion and passage of such device relative an inner catheter insertion lumen may thus be improved for delivery of the device to a target site inside the patient.

Alternatively, or in addition, in some examples, the frame may be intrinsically curved in a superior direction. The intrinsic superior curvature can be throughout the length of the frame or at portions of the frame. For example, an intrinsic superior curve can be at each end of the frame (e.g., the proximal region and the distal region) but could also be at either end of the frame (e.g., the proximal region or the distal region), while the central portion of the frame can be planar (e.g., the filter can be substantially planar with slight intrinsic superior curves having a height that is less than the width of the frame). This configuration allows the installed device to respond to upward forces (e.g., forces induced by blood-flow or manual maneuvering via a catheter within the aortic arch) by flattening the intrinsically curved portions at the proximal and distal ends and bending the central region inferiorly, adopting a general curvature in alignment with the aortic arch. The general curvature may be in advantageous (tension) force against the inner aortic wall tissue. In the installed configuration, there may be an open space between the central portion(s) of the frame and the superior wall of the aortic arch, and/or there may be an open space between the superior face of the filter and the superior wall of the aortic arch. The installed configuration is self-stabilizing as a result of the intrinsically superior curved portion(s), which tend to return to their intrinsic conformation, providing an outward (i.e., distal and proximal) force on the walls of the ascending and descending aortas. In some cases, the superior face of the filter and/or frame contacts the walls of the ascending and/or descending aorta. In other cases, only the edge of each end of the frame may contact the aortic walls. Forces provided to the aortic walls by the proximal and distal ends of the frame are governed by various physical parameters, which are understood by a person of skill in the art. For example, varying the stiffness (e.g., by varying the type of material of the frame, or by otherwise varying the elastic modulus of the frame, e.g., by varying the thickness of the frame in one or more dimensions) will alter the forces exerted by the frame. Varying the length and curvature of the frame will likewise change the forces exerted by the frame to the aortic walls. Forces transmitted by the filter to the arterial walls are sufficient to hold the filter in its installed position without damaging the aortic walls (e.g., upon removal of the device). The material of the filter may also contribute to the flexure of the frame and/or forces transmitted by the frame to the aortic walls.

The device may also include one or more superior stabilizers and/or one or more inferior stabilizers. Superior and/or inferior stabilizers can be attached to the frame, e.g., at or near the central region of the frame to provide stability in one or more dimensions and/or to provide resistance to rotation (e.g., rolling) about a transverse axis (e.g., in the direction of blood-flow). A stabilizer (e.g., an inferior stabilizer) can additionally or alternatively provide lift to the frame or filter, e.g., by contacting and exerting an inferior force on the wall of the aortic arch. Such lift can enhance the inferior curvature of the installed frame and filter. A device of the disclosure features two inferior stabilizers, which are oppositely attached at a front and a back central region of the filter, located proximal to the ascending aorta upon installation of the device.

A device of the disclosure may additionally feature a superior stabilizer (such as one superior stabilizer) attached at a point on the front central portion of the filter and the corresponding point on the back central portion of the filter, distal to the attachment points of the front and back inferior stabilizers. The superior stabilizer spans the width of the filter as a loop over the superior face of the filter. The superior stabilizer is configured to contact a wall (e.g., a proximal wall) of an innominate artery. A superior stabilizer of the disclosure may include one or more bends (e.g., 1, 2, 3, 4, 5, 6, or more bends, e.g., intrinsic bends, e.g., proximal intrinsic bends). A superior stabilizer can include four intrinsic proximal bends (e.g., two sets of bends having symmetry about a coronal plane), two of which enable the superior stabilizer to distally extend from its central connection points on the filter and bend superiorly to enter the innominate artery. Two additional intrinsic proximal bends at the superior end of the superior stabilizer form a transverse distal curve, which optionally has a radius of curvature similar to the radius of the adjacent arterial wall to optimize contact with the arterial wall (e.g., by maximizing contact area and evenly distributing contact forces throughout).

The filter prevents particles (e.g., emboli) typically having a dimension between about 50 μm and about 5 mm (e.g., 50 μm, 100 μm, 200 μm, 300 μm, 400 μm, 500 μm, 750 μm, 1 mm, 2 mm, 3 mm, 4 mm, or 5 mm) in an aorta from passing into blood vessels (e.g., innominate brachiocephalic) artery, left common carotid artery, or left subclavian artery) supplying blood to the brain. Accordingly, one or more lateral dimensions of the pores of the filter can be between about 50 μm and about 5 mm (e.g., 50 μm, 100 μm, 200 μm, 300 μm, 400 μm, 500 μm, 750 μm, 1 mm, 2 mm, 3 mm, 4 mm, or 5 mm). The filter can be, e.g., a mesh made from a plurality of fibers made of polymer, nylon, nitinol, or metal, or a combination thereof. Fibers can be from about 20 to 50 μm in thickness. Alternatively, the filter can be a perforated film. When a perforated film is present, the pores formed in the perforated film may include pores of varied or unvaried shape (e.g., rectilinear or rhomboid pores), have a varied or constant density across the film, and/or have a constant or varied size. The size of the pores of the filter allows passage of blood cells (e.g., red blood cells (erythrocytes), white blood cells (leukocytes), and/or platelets (thrombocytes)) and plasma, while being impermeable to particles (e.g., emboli) larger than the pore dimensions. Emboli filtered by the mesh of the filter of the present disclosure are typically particles larger in one or more dimensions than an aperture of the mesh of the filter.

The frame may be substantially elliptical, oblong or elongated in shape. Alternatively, other shapes may be used, such as circular or rectangular. Because the aortic anatomy can vary between individuals, examples of the intra-aortic device of the disclosure are shaped to adapt to a variety of aortic anatomies.

The size of the device may be pre-sized and pre-formed to accommodate various patient groups (e.g., children and adults) or particular aortic anatomy. The frame may be substantially planar and have a length from about 80 mm and 90 mm, a width from about 20 mm to 35 mm, and a height from about 2 mm to 30 mm. The length of the filter may be from approximately 80 mm to 90 mm, or otherwise as necessary to approximate a distance between an upper wall of an ascending aorta of a subject, distal to an opening of an innominate artery, and an upper wall of a descending aorta of a subject, proximal to an opening of a left subclavian artery.

The length of the filter may depend on other factors, such as the position of the intrinsically bent portion(s) along the length of the frame, the length of the distal and/or proximal bows, and the curvature of the intrinsic bend(s). The width of the filter may be from 20 mm to 35 mm or otherwise may approximate an internal diameter or cross-sectional chord of an aorta of a subject. The frame, stabilizer(s), or catheter(s) of the device can be fabricated in whole or in part from, e.g., nitinol or metal wire, superelastic or shape memory alloy material, readily malleable material, or polymer, e.g., nylon. The metal wire may include, e.g., tantalum or platinum.

For positioning in an aorta, the device of the disclosure can be attached to a catheter according to methods known in the art or by a connector mechanism, wherein a distal latch connects the filter to a catheter by attaching to a proximal latch.

Various catheters can be used as part of the present disclosure. Any catheter known in the art to be configured for guiding medical instruments through vasculature can be used (e.g., stent installation catheter, ablation catheter, or those used for transcatheter aortic valve implantation (TAVI) or percutaneous aortic valve replacement (PAVR) procedures, e.g., as described in U.S. Pat. No. 5,026,366). Additionally or alternatively, the device can include a pigtail catheter, which may be of size 6F or smaller (e.g., 1F, 2F, 3F, 4F, 5F, or 6F) and include a radiopaque material to facilitate tracking the progress of various elements of the device. Other catheters that can be used as part of the disclosure include any catheter used in procedures associated with a risk of embolism, which would benefit by including an intravascular filter as part of the procedure.

A device of the disclosure can incorporate radiopaque elements. Such radiopaque elements can be affixed to, or incorporated into the device. For example, portions of the frame, stabilizers, filter, or catheter can be constructed of OFT wire. Such wire can contain, e.g., a core of tantalum and/or platinum and an outer material of, e.g., nitinol.

Methods

The disclosure provides a method of preventing passage of an emboli from an aorta into an artery branching from the aorta by installing a device of the disclosure in the aorta. When the device is installed, one or more (e.g., 1, 2, 3, 4, or more) portions of the frame having an intrinsic curve may be flattened.

A device of the disclosure can be inserted into a vessel (e.g., a peripheral vessel, e.g., a femoral artery) according to known techniques. For example, in its longitudinally collapsed configuration, the device can be packed within an introducer sheath configured to carry the device across the skin and through the vessel to the aortic arch. A guidewire can be used to guide the introducer sheath and device through the vasculature to the aortic arch, according to known methods. For example, the guidewire can be inserted into the peripheral vessel, e.g., a femoral artery by passing it through a needle (e.g., a Seldinger needle). The needle can then be removed to allow the introducer sheath to be fed over the guidewire into the vessel. The device can then be manually advanced, within the introducer sheath, over the guidewire to its operative position at the aortic arch. If needed to expand the vessel and create space for the advancing introducer sheath, a dilator tip (e.g., a J tip wire) may be configured on the tip of the guidewire or concurrently advanced through the vasculature distal to the device.

Upon reaching the desired location within the aortic arch, the introducer sheath may be retracted, allowing the device to expand into its operative configuration. For example, the intrinsically bent regions of the frame may be flattened relative to its intrinsic state to secure the filter over the openings of the arteries branching from the aorta, and the one or more stabilizers may extend to contact their respective vessel walls. To position or reposition the device in the aortic arch after removal of the introducer sheath, the device may be manually adjusted by manipulating the guidewire or the catheter. To enable visualization and facilitate positioning of the device, a pigtail catheter may also be loaded within the introducer sheath, using components known in the art and/or described above.

A device of the present disclosure can be used for protection of the brain from particles, e.g., emboli, prior to, during, and/or after an invasive intracardiac procedure, such as balloon aortic valvuloplasty, balloon mitral valvuloplasty, electrophysiological studies, with or without ablation of ectopic rhythmic sites, insertion of automatic defibrillators, percutaneous valve repair or replacement (e.g., PAVR), or other procedures. The device can be used, for example, in subjects with severe aortic atheroma for brain protection during routine heart catheterization, or for endovascular "cleaning" of atheromatous or thrombotic material. The device could be used in subjects with high risk or propensity to form intracardiac clots, (e.g., subjects with hematological disease), subjects with arrhythmia of the heart, artificial heart subjects, assist-device subjects, mechanical valve replacement subjects, subjects following intracardiac repair of a pathology, or subjects with congenital heart disease (e.g., patent foramen ovale). Other applications of blood particulate filters, medical procedures that benefit from the use of blood particulate filters, and patients at risk of damage resulting from blood particulates are known in the art.

A device of the disclosure can also be used temporarily for acute conditions. For example, the device may be inserted temporarily to protect against cardio embolic stroke or embolic stroke. The device of the disclosure may be used to reduce the risk of damage resulting from blood particulates, such as emboli in subjects from suffering conditions associated with an elevated risk thereof, such as acute myocardial infarction (AMI). Thus, the device may be inserted for the duration of a procedure or treatment.

A device of the disclosure may be used in conjunction with one or more pharmaceutical compositions, such as a drug known to treat endocarditis or blood clots.

EXAMPLES

In the following description, various examples of the disclosure will be described. For purposes of explanation, specific examples are set forth in order to provide a thorough understanding of at least one example of the disclosure. However, it will also be apparent to one skilled in the art that other examples of the disclosure are not limited to the examples described herein. Furthermore, well-known features or processes may be omitted or simplified in order not to obscure examples of the disclosure described herein.

Reference is made to FIG. 1A, a schematic diagram of a side-view of a device 100 including a frame 10, and catheter attachment 15 in an intrinsic configuration. The device 100 includes a frame 10 to hold a filter and define the area, shape, and curvature of the filter. In this diagram, the back lateral portion of the frame 10 is hidden from view by the front lateral portion of the frame 10. The frame 10 includes intrinsic superior curves 13, 14 at both the distal end 11 and the proximal end 12. The proximal end 12 of the frame 11 is angled at a point of connection to a catheter. Catheter attachment 15 may be a stem connected to the frame and may move freely in 360 degrees.

Alternatively, in some examples, the catheter attachment 15 may be restricted, such as having a fixed angle at a point of connection to a catheter, such that a catheter runs substantially parallel to the central region of the frame.

Figure 1B:
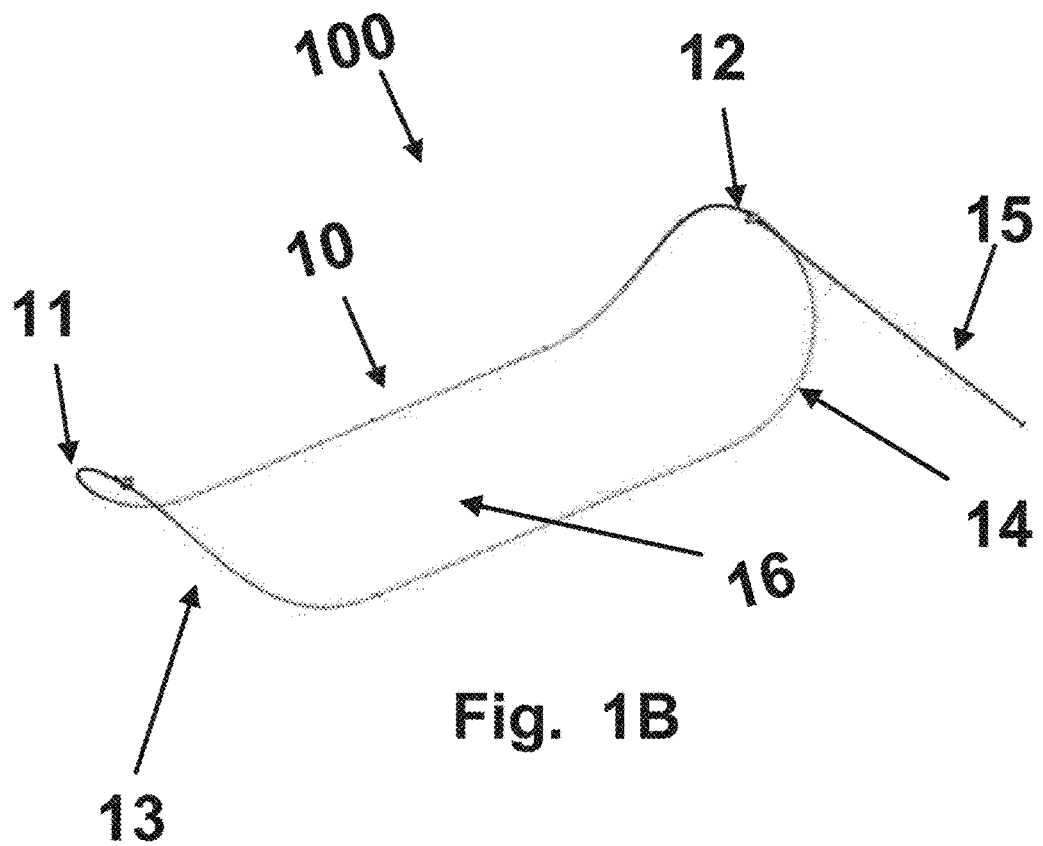

Reference is made to FIG. 1B, a 3-dimensional schematic diagram of a device 100 in FIG. 1A including a frame 10, and catheter attachment 15 in an intrinsic configuration. The device 100 includes a frame 10 to hold a filter 16 and define the area, shape, and curvature of the filter 16. In this diagram, the back lateral portion of the frame 10 is hidden from view by the front lateral portion of the frame 10. The frame 10 includes intrinsic superior curves 13, 14 at both the distal end 11 and the proximal end 12. The proximal end 12 of the frame 11 is angled at a point of connection to a catheter. Catheter attachment 15 may be a stem connected to the frame and may move freely in 360 degrees.

The shape of the filter 16 is defined by the frame 10 (i.e., the periphery of the filter 16 is attached to the frame 10, such that flexure of the frame 10 induces a change in shape (e.g., curvature) of the filter 16. The filter 16 of the device of FIGS. 1A and 1B may be inferiorly concave. This concavity allows the filter 16 to lie securely against the aorta wall upon installation in an aorta.

Figure 2A:
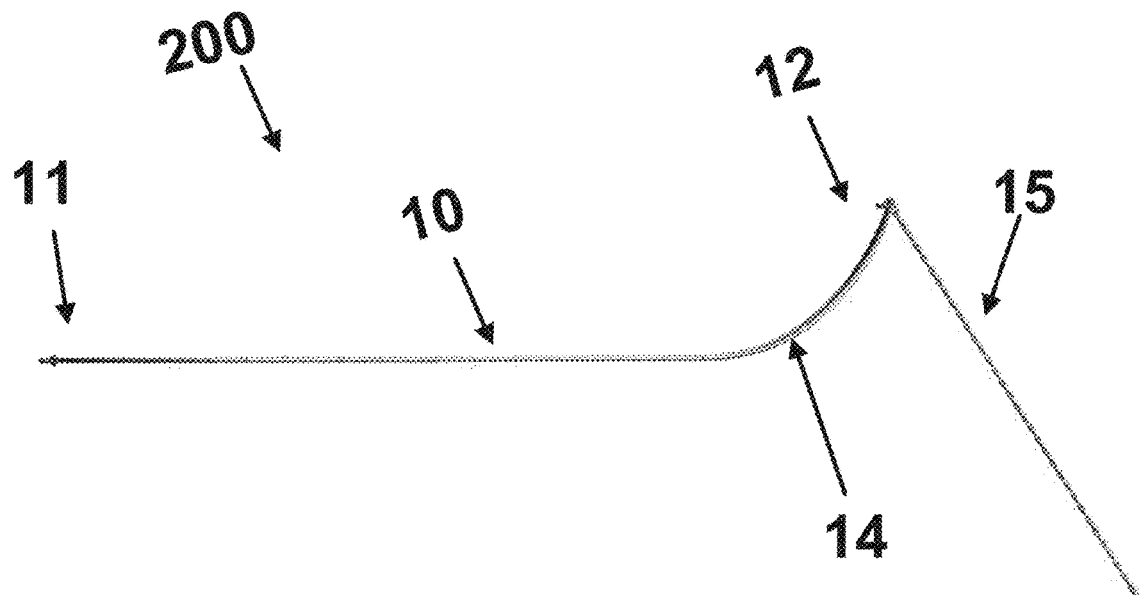
FIGS. 2A and 2B are schematic diagrams illustrating a frame and catheter attachment in an intrinsic configuration with a proximal superior bend.

Reference is made to FIG. 2A a schematic diagram of a side-view of a device 200 including a frame 10, and catheter attachment 15 in an intrinsic configuration. The device 200 is similar to the device 100 illustrated in FIGS. 1A and 1B except that in this intrinsic configuration, the device 200 has a proximal superior bend 14 at a proximal end 12 while the distal end 11 is flat. Alternatively, in some examples of the device 200, the intrinsic configuration of the device 200 has a distal superior bend 13 at a distal end 11 while the proximal end 12 is flat.

Figure 2B:
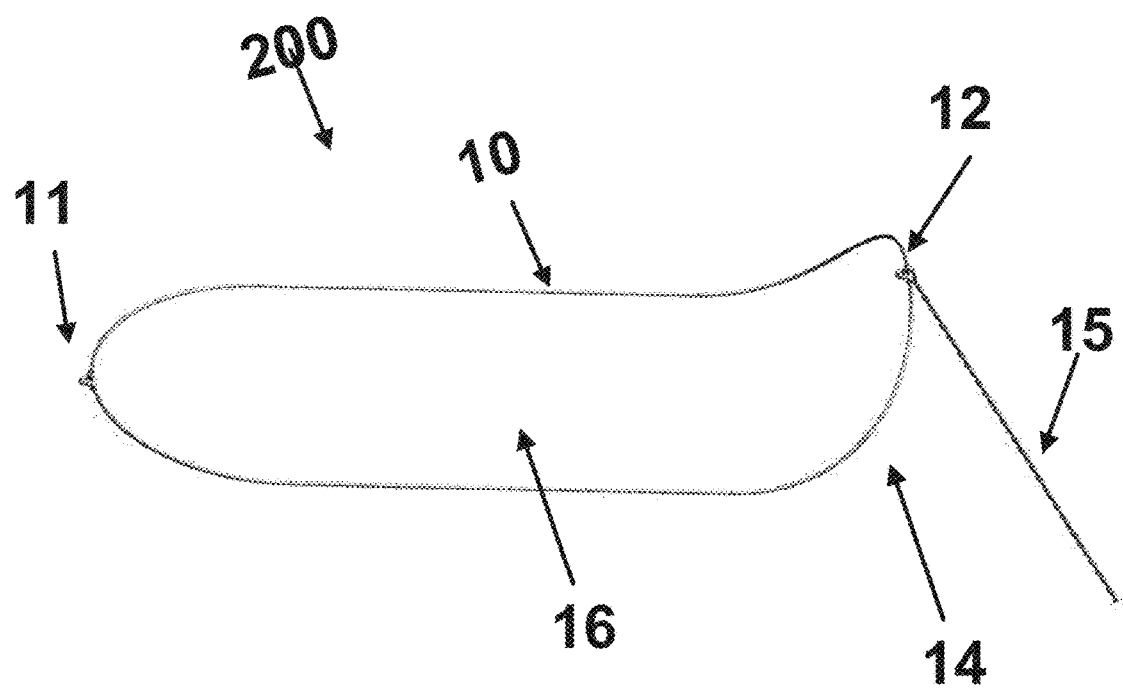

Reference is made to FIG. 2B, a 3-dimensional schematic diagram of a device 200 in FIG. 1A including a frame 10, and catheter attachment 15 in an intrinsic configuration. The device 200 includes a frame 10 to hold a filter 16 and define the area, shape, and curvature of the filter 16.

The shape of the filter 16 is defined by the frame 10 (i.e., the periphery of the filter 16 is attached to the frame 10, such that flexure of the frame 10 induces a change in shape (e.g., curvature) of the filter 16. The filter 16 of the device of FIGS. 2A and 2B may be inferiorly concave. This concavity allows the filter 16 to lie securely against the aorta wall upon installation in an aorta.

Figure 3A:
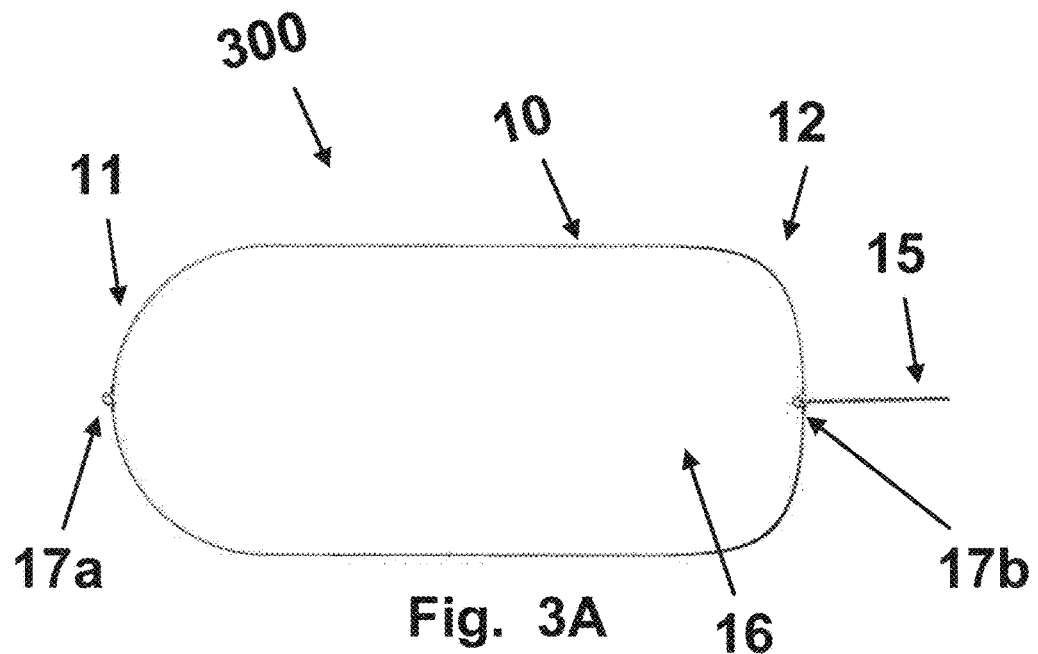
FIGS. 3A and 3B are schematic diagrams illustrating a top view of a frame and catheter attachment.
Figure 3B:
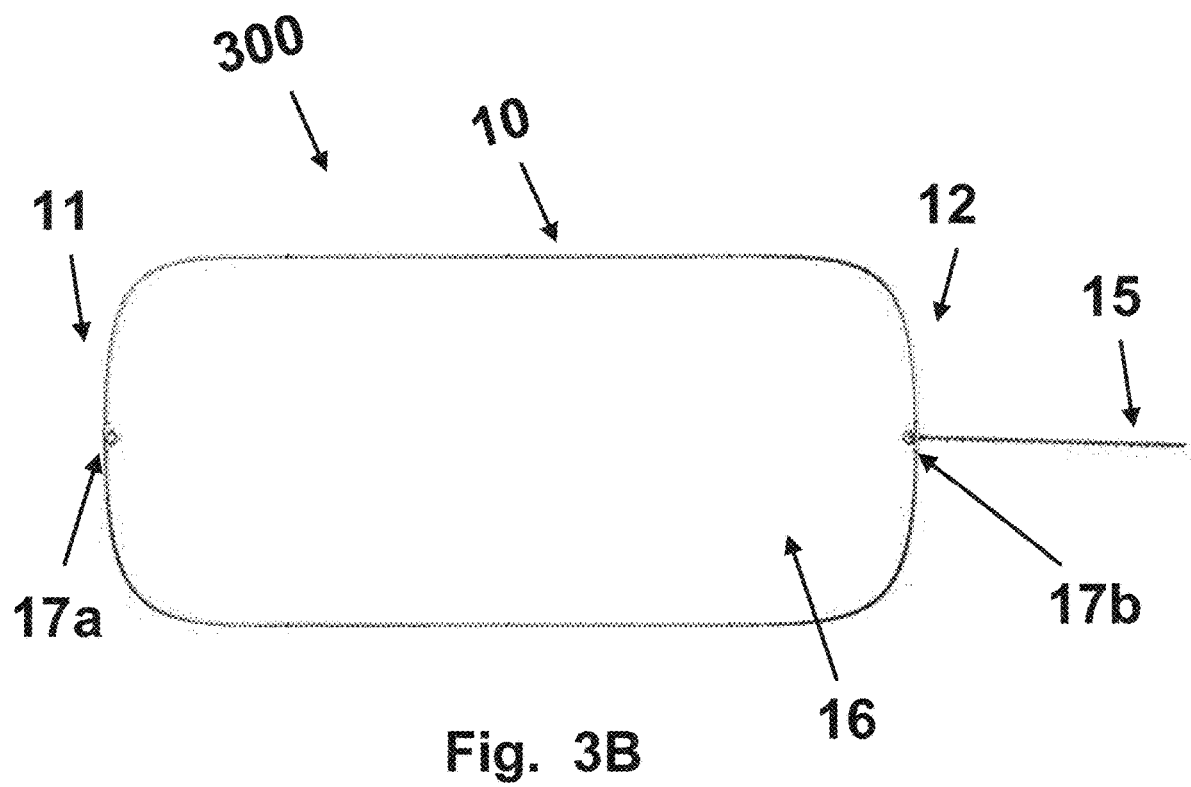

FIGS. 3A and 3B are schematic diagrams illustrating a top view of a frame 10 and catheter attachment 15 having different elongated shapes. The device 300 may either have an intrinsic configuration as illustrated in FIGS. 1A, 1B, 2A, 2B, but could also, in some examples, have a flat configuration.

In FIGS. 3A and 3B crimp member, 17a and 17b are illustrated. The device 300 may have a crimp member 17a and 17b at both the distal end 11 and at the proximal end 12. Alternatively, in some examples of the device 300, a crimp member 17a and 17b is only arranged at either the distal end 11 or at the proximal end 12. A crimp member 17a, 17b is used to facilitate the crimping of the device, such as collapsible the frame 10 along a longitudinal axis of the device 300.

In the FIGS. 3A and 3B, the crimp members 17a, 17b are illustrated as loops made from the frame 10. The members could have other shapes such as triangular, or a nose or tongue shape formed by bending the frame 15 giving the nose or tongue a shape with a width narrower than the width of the frame 15.

The crimp members 17a, 17b may either be formed to be protruding outwards, as the distal crimp 17a in FIG. 3A, or formed to be protruding inwards, as the distal crimp 17a in FIG. 3B.

Crimp members 17a, 17b arranged to protrude inwards are it improves attachment of the filter 16 to the frame 10. Also, having the crimp members 17a, 17b arranged to protrude inwards improves the contact between the frame 10 and the walls of the aortic arch as there is nothing protruding or extending further than the frame 10.

Additionally, in some examples, the catheter attachment 15 may be attached to the frame 15 via a proximal crimp member 17b, thereby allowing the catheter attachment 15 to move freely in 360 degrees.

Figure 4:
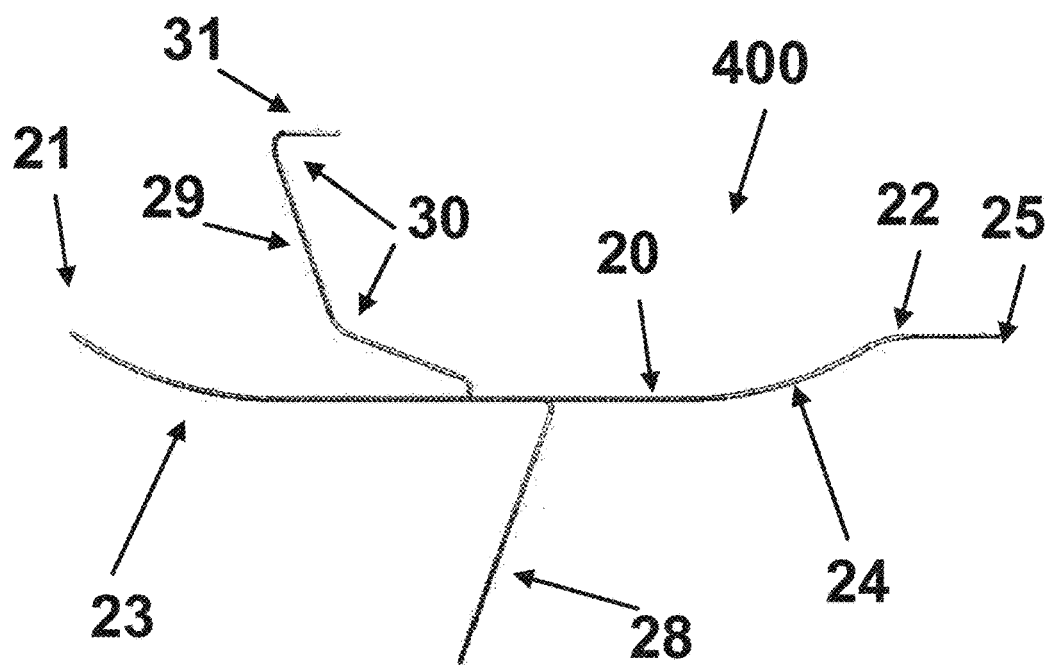
FIG. 4 is a schematic diagram illustrating a side-view of a frame, stabilizers, and catheter attachment of an example in their intrinsic configuration.

Reference is made to FIG. 4, a schematic diagram of a side-view of a frame 20, stabilizers 28, 29, and catheter attachment 25 in their intrinsic configuration. The device 400 includes a frame 20 to hold a filter and define the area, shape, and curvature of the filter. In this diagram, the back lateral portion of the frame 20 is hidden from view by the front lateral portion of the frame 20. The frame 20 includes intrinsic superior curves 23, 24 at both the distal 21 end and the proximal end 22. In the illustrated example, the proximal end 22 of the frame 20 is angled at a point of connection 25 to a catheter, such that a catheter runs substantially parallel to the central region of the frame 10.

Alternatively, in some examples, the device 400 only has a superior bend, such as a superior distal bend 23 or a superior proximal bend 24.

Additionally, in some examples, the frame 20 of the device 400 has crimp members as described in connection for FIGS. 3A and 3B.

The device 400 includes stabilizers 28, 29 that are configured to resist movement of the device upon installation in a patient's aorta. A front inferior stabilizer 28 is attached to the frame 20 at a central region of a front lateral portion of the frame 20. A back lateral stabilizer is hidden from view by the front inferior stabilizer 28, and is symmetrically attached to the frame at a central region of a back lateral portion of the frame 20. The inferior stabilizers 28 intrinsically point distally. A superior stabilizer 29 is attached to the frame 20 at a central region of opposing (e.g., back and front) lateral portions of the frame 20. The back region of the superior stabilizer 29 is hidden from view by the front region, as it is symmetrical about a coronal plane. The superior stabilizer 29 may be attached to the frame 20 distally from the attachment point of the inferior stabilizers 28 to the frame 20. The superior stabilizer 29 comprises four intrinsic proximal bends 30 (two on the front portion and two on the back portion) and a transverse curve 31 connecting the front portion to the back portion of the superior end of the superior stabilizer 29.

Figure 5:
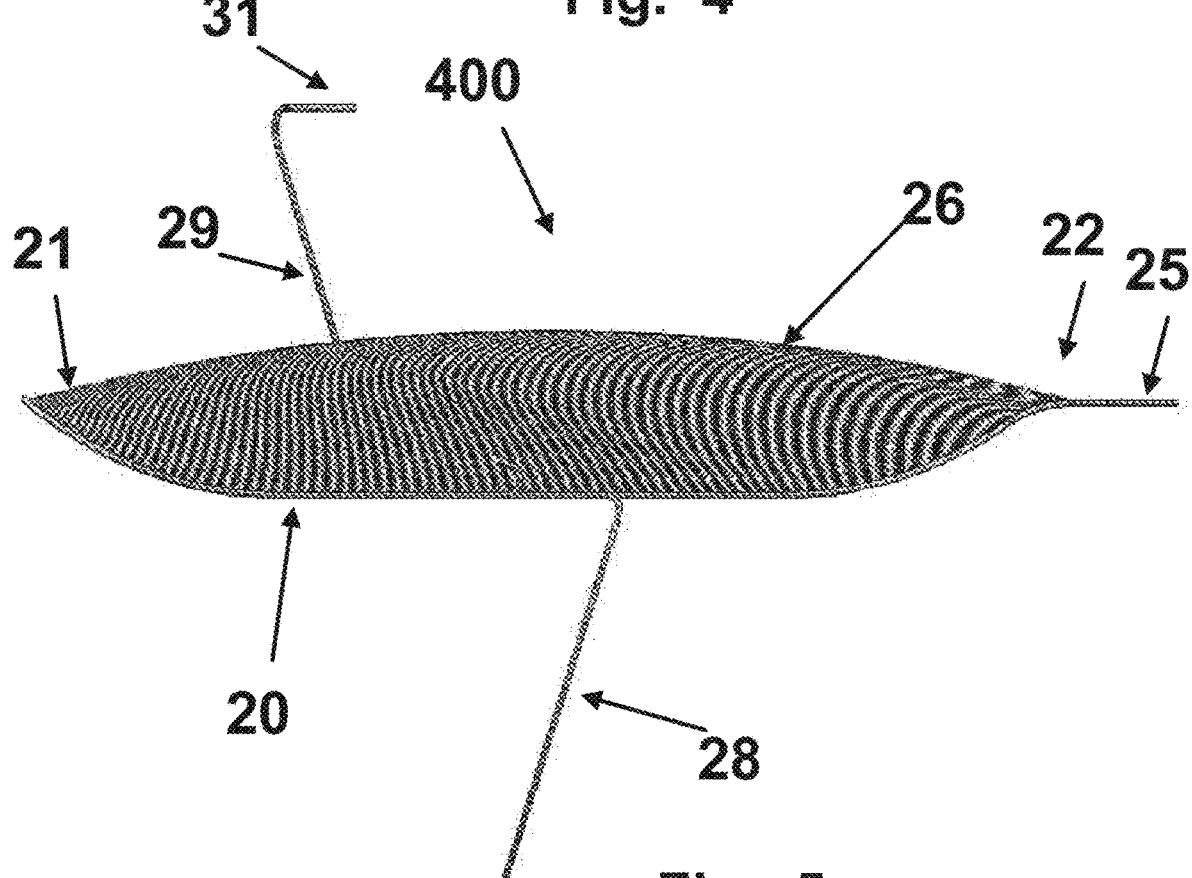
FIG. 5 is a schematic diagram illustrating a side-view of an example of the device of the disclosure, including the filter.

Reference is made to FIG. 5, a schematic diagram of a side-view of the device 400 of the disclosure. This diagram depicts the frame 20, stabilizers 28, 29, and catheter attachment 25 as in FIG. 4, and additionally shows the filter 26. The shape of the filter 26 is defined by the frame (i.e., the periphery of the filter 26 is attached to the frame 20, such that flexure of the frame 20 induces a change in shape (e.g., curvature) of the filter 26. The filter 26 of the device of FIG. 4 may be inferiorly concave. This concavity allows the filter 26 to lie securely against the aorta wall upon installation in an aorta.

Figure 6:
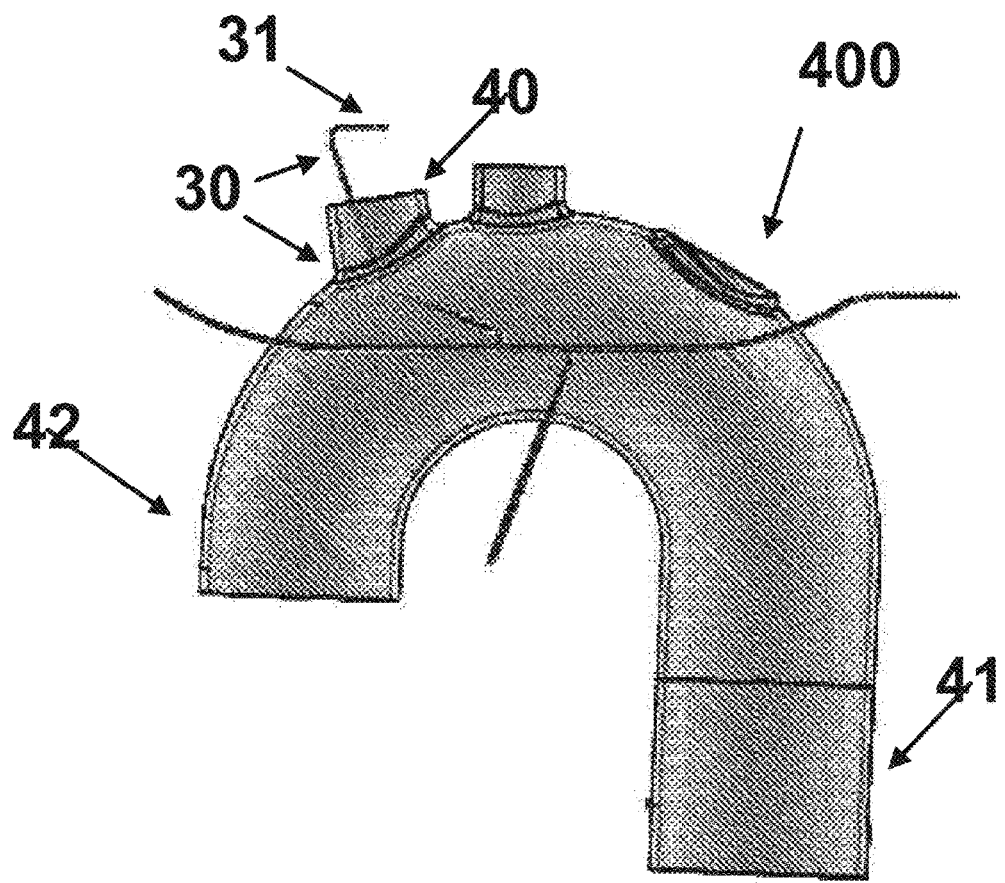
FIG. 6 is a schematic diagram overlying the side-view of FIG. 4 onto an aorta, depicting the spatial relationship between the aortic space and the intrinsic configuration of an example of the frame, stabilizers, and catheter.

Reference is made to FIG. 6, a schematic diagram overlying the side-view of the device 400 of FIG. 4 onto an aorta, depicting the spatial relationship between the aortic space and the intrinsic configuration of the frame, stabilizers, and catheter. The same relationship would exist for a device without the stabilizers, such as a device as illustrated in FIGS. 1A, 1B, 2A, 2B, 3A and 3B.

In the absence of lateral restriction by the aortic walls, the plane of the frame is substantially transverse going from the ascending aorta 42 to the descending aorta 41. The superior stabilizer contacts the proximal wall 40 of the innominate artery. The intrinsic proximal bends 30 and the transverse curve 31 optimize contact of the superior stabilizer with the proximal wall 40 of the innominate artery. The inferior stabilizers, shown in their intrinsic positions overlying the inferior wall of the aortic arch, are forced to bend distally upon installation of the device in the aorta and contact the proximal wall of the ascending aorta or the inferior wall of the aortic arch.

Figure 7:
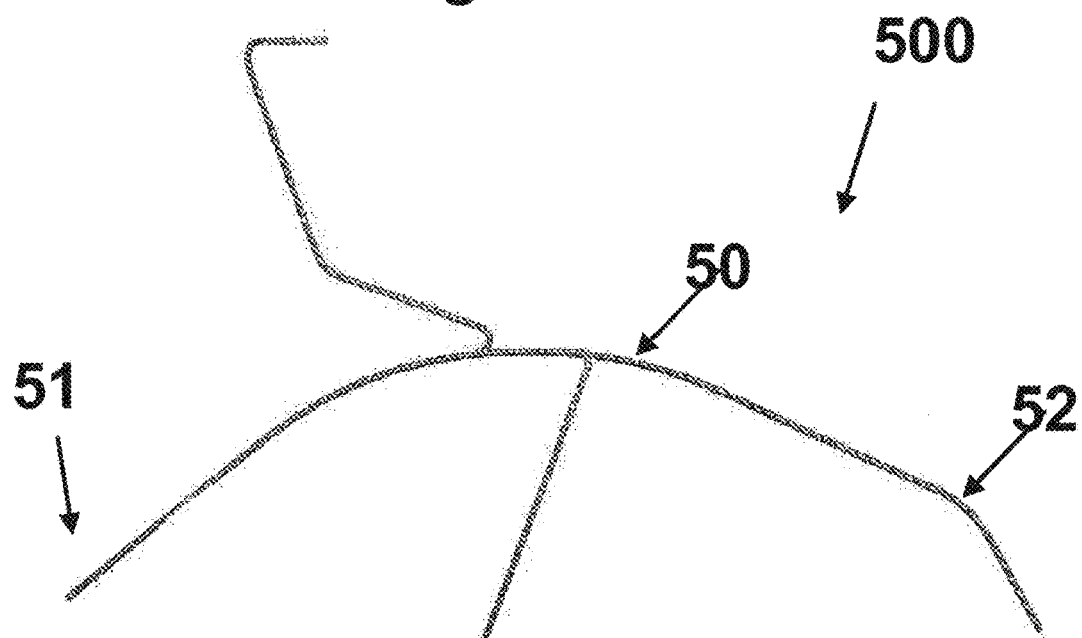
FIG. 7 is a schematic diagram illustrating a side-view of a an example of a frame, stabilizers, and catheter attachment in their installed configuration.

Reference is made to FIG. 7, a schematic diagram showing a side-view of the installed configuration of a device 500 including the frame 50, stabilizers, and catheter attachment of FIG. 4. The frame 50 is inferiorly bent, such that the central portion of the frame 50 is superior to the distal 51 end and the proximal end 52 of the frame 50. The central attachment points of the superior and inferior stabilizers allow the stabilizers to remain in substantially the same orientation as when the frame is in its intrinsic configuration.

The same relationship as illustrated in FIG. 6 would exist for a device without the stabilizers, such as a device as illustrated in FIGS. 1A, 1B, 2A, 2B, 3A and 3B.

Figure 8:
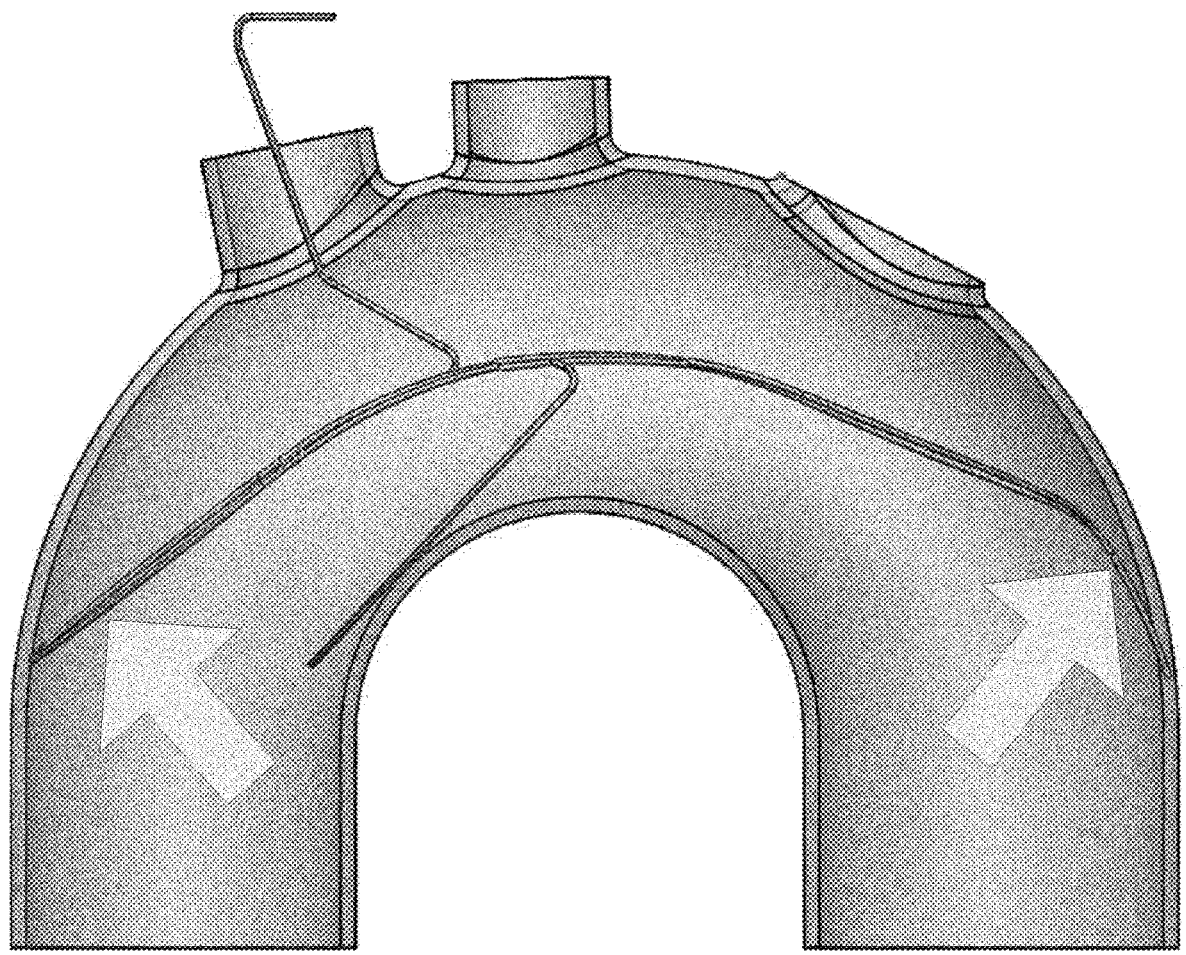
FIG. 8 is a schematic diagram overlying the side-view of FIG. 7 onto an aorta.

Reference is made to FIG. 8, a schematic diagram overlying the side-view of FIG. 7 onto an aorta. Upon installation of the device, the aortic walls constrain the frame, inducing the frame to bend inferiorly, such that the central portion of the frame is superior to the distal and proximal ends of the frame. This flexure provides outward force on the aortic walls (white arrows), enhancing the stability of the frame in a position suitable to prevent emboli from entering arteries branching from the aorta.

As long as the above described forces are provided or providable by devices and/or procedures using such devices, alternatively, instead of an outer frame, the shape and function of devices described herein may be provided by frameless design aware to the skilled person. Alternative or additional designs may under the same force providing requirements include yokes, spokes or similar arrangements—alternatively or in addition to a frame as described in detail above.

It will be appreciated by persons skilled in the art that examples of the disclosure are not limited by what has been particularly shown and described above. Various modifications of the described modes for carrying out the disclosure are intended to be within the scope of the disclosure.

What is claimed is:

1. An intra-aortic device comprising a filter member and a frame made from at least one wire and defining the shape of the filter member;
   a first crimping member arranged at a distal region of the frame and the first crimping member is formed to protrude inwards;
   a catheter attachment having an elongated shape arranged at a proximal region of the frame wherein the catheter attachment is arranged to move freely in 360 degrees.

2. The intra-aortic device of claim 1, wherein a second crimping member is arranged at the proximal region.

3. The intra-aortic device of claim 2, wherein the catheter attachment is attached to the frame via the second crimping member.

4. The intra-aortic device of claim 2, wherein the second crimping member is a loop formed of the frame.

5. The intra-aortic device of claim 2, wherein the second crimping member is formed to protrude inwards.

6. The intra-aortic device of claim 2, wherein the second crimping member facilitate collapsing the frame along a longitudinal axis of frame.

7. The intra-aortic device of claim 1, wherein the first crimping member is a loop formed of the frame.

8. The intra-aortic device of claim 1, wherein the first crimping member facilitate collapsing the frame along a longitudinal axis of frame.

9. The intra-aortic device of claim 1, wherein the filter member is configured to span more than one artery branching from the aorta.

10. The device of claim 1, wherein the frame is configured to be held in contact with both an ascending aorta and a descending aorta, simultaneously.

11. The intra-aortic device of claim 1, wherein the filter member comprises a plurality of woven fibres forming a mesh.

12. The intra-aortic device of claim 1, wherein the filter member comprises pores having a median pore size of less than 1 mm.

13. The intra-aortic device of claim 1, wherein the frame is made from nitinol.

14. The intra-aortic device of claim 1, wherein the frame and filter member have a circular, elliptical or elongated shape.

15. The intra-aortic device of claim 1, wherein the frame is a spring ring wire.

16. The intra-aortic device of claim 1, wherein there is nothing extending further than the frame.

17. The intra-aortic device of claim 1, wherein the catheter attachment is a stem.

18. The intra-aortic device of claim 1, wherein a plane of the frame is substantially transverse going from an ascending aorta to a descending aorta.

19. The intra-aortic device of claim 1, wherein the filter member is made from a polymer.

20. The intra-aortic device of claim 1, wherein at least one radiopaque element is affixed to or incorporated into portions of the frame.

21. The intra-aortic device of claim 1, wherein the frame is encircling the filter.

* * * * *